United States Patent
Frezza

(12) 
(10) Patent No.: US 6,398,031 B1
(45) Date of Patent: Jun. 4, 2002

(54) VIAL FOR PACKAGING A LIQUID FOR MEDICAL USE

(76) Inventor: Pierre Frezza, 455A route du Bas Privas, F-69390 Charly (FR)

( * ) Notice: Subject to any disclaimer, the term of this patent is extended or adjusted under 35 U.S.C. 154(b) by 0 days.

(21) Appl. No.: 09/674,664

(22) PCT Filed: Mar. 17, 2000

(86) PCT No.: PCT/FR00/00670

§ 371 (c)(1),
(2), (4) Date: Nov. 21, 2000

(87) PCT Pub. No.: WO00/57834

PCT Pub. Date: Oct. 5, 2000

(30) Foreign Application Priority Data

Mar. 25, 1999 (FR) .............................. 99 03901

(51) Int. Cl.[7] .................................. A61M 5/32
(52) U.S. Cl. ...................... 206/571; 206/365; 604/192
(58) Field of Search ................. 206/222, 210, 206/363, 364, 365, 366, 571; 604/192, 198, 201, 205, 263

(56) References Cited

U.S. PATENT DOCUMENTS

| | | | | |
|---|---|---|---|---|
| 2,400,722 A | | 5/1946 | Swan .......................... 206/210 |
| 3,397,694 A | * | 8/1968 | Ogle ........................... 206/365 |
| 3,416,657 A | * | 12/1968 | Sorensen, Jr. et al. ...... 206/365 |
| 3,563,373 A | | 2/1971 | Paulson et al. ............. 206/365 |
| 3,696,579 A | | 10/1972 | Narusawa et al. ............. 53/428 |
| 3,940,003 A | * | 2/1976 | Larson ........................ 206/363 |
| 3,977,555 A | * | 8/1976 | Larson ........................ 206/363 |
| 4,084,588 A | * | 4/1978 | Koenig ....................... 604/205 |
| 4,390,016 A | | 6/1983 | Riess .......................... 604/194 |
| 4,401,432 A | | 8/1983 | Schwartz .................... 604/190 |
| 4,576,211 A | * | 3/1986 | Valentini et al. ............. 604/201 |
| 4,845,923 A | * | 7/1989 | Donovan .................... 206/365 |
| 6,070,623 A | * | 6/2000 | Aneas ........................ 604/201 |
| 6,258,078 B1 | * | 7/2001 | Thilly ........................ 604/201 |

FOREIGN PATENT DOCUMENTS

WO    WO 96/00556    1/1996

* cited by examiner

Primary Examiner—Jim Foster
(74) Attorney, Agent, or Firm—Oliff & Berridge, PLC.

(57) ABSTRACT

This vial comprises a tubular body (2) made of synthetic material exhibiting two chambers which are isolated in a sealed manner by a puncturable membrane (7) or a removable or tearable wall, one of which chambers (3) contains the liquid and the other (4) of which chambers contains a hypodermic needle (16), the pointed part of which points towards the puncturable membrane or removable or tearable wall, and the other end of which is fitted with means (17) of connection to a syringe body.

8 Claims, 4 Drawing Sheets

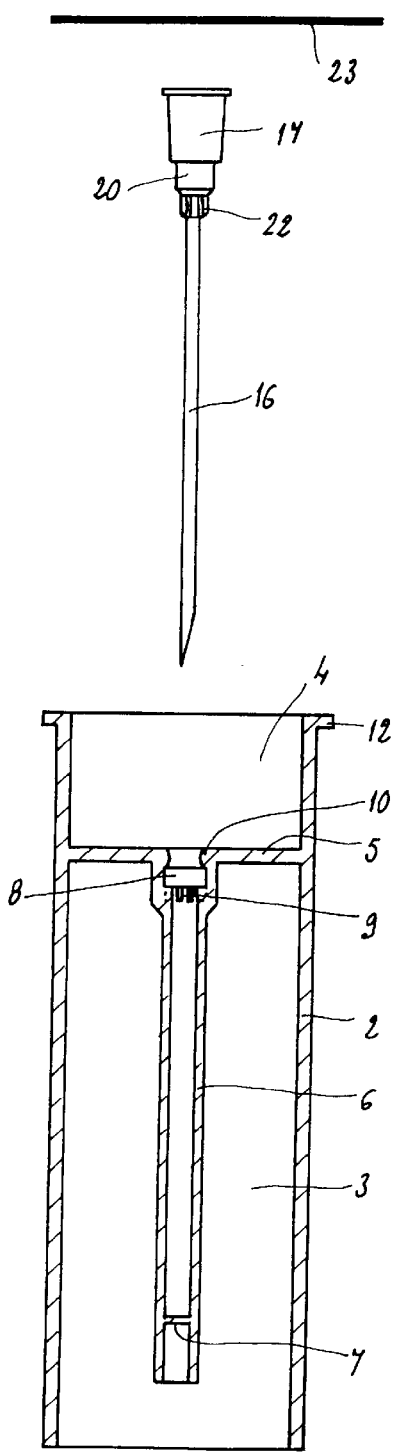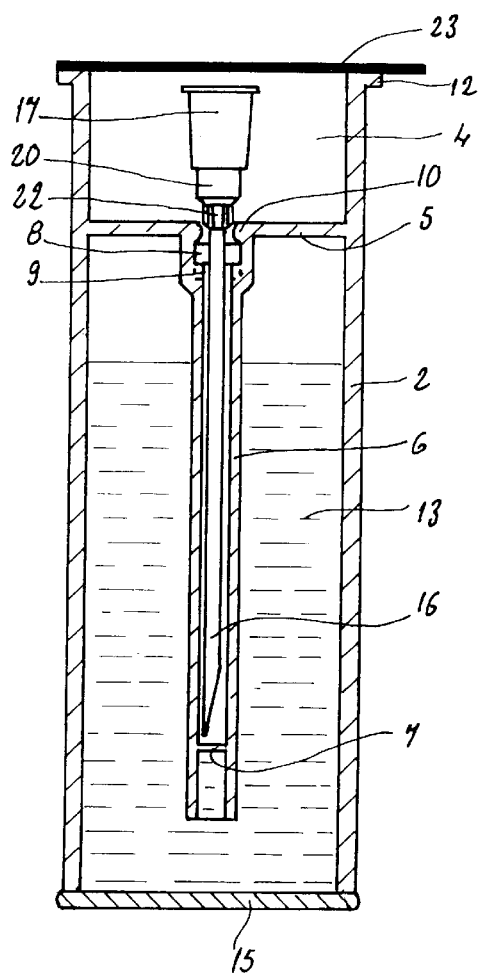

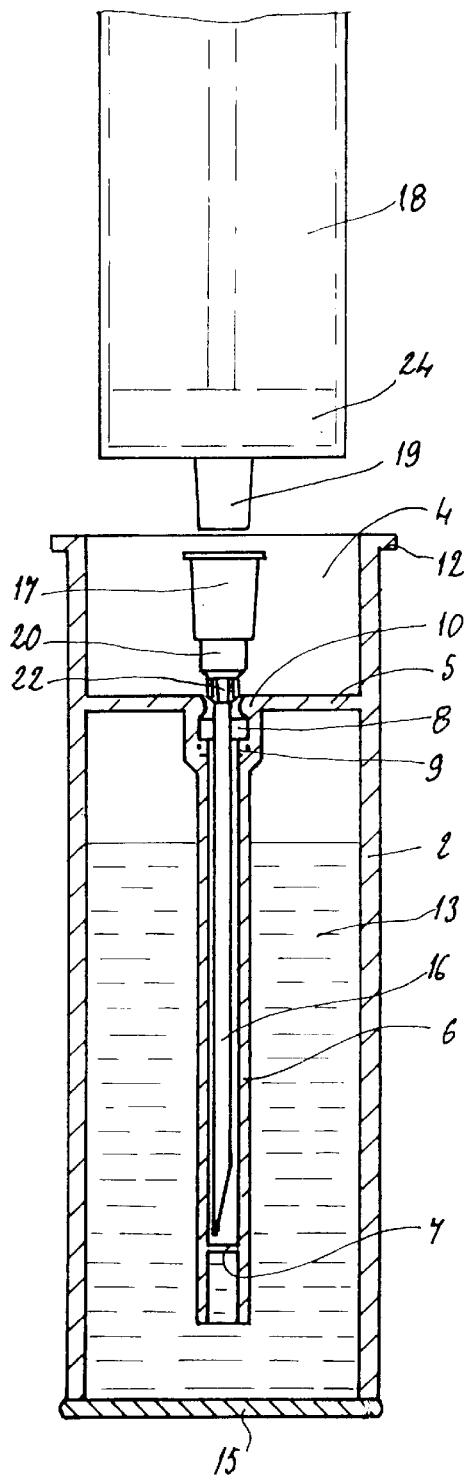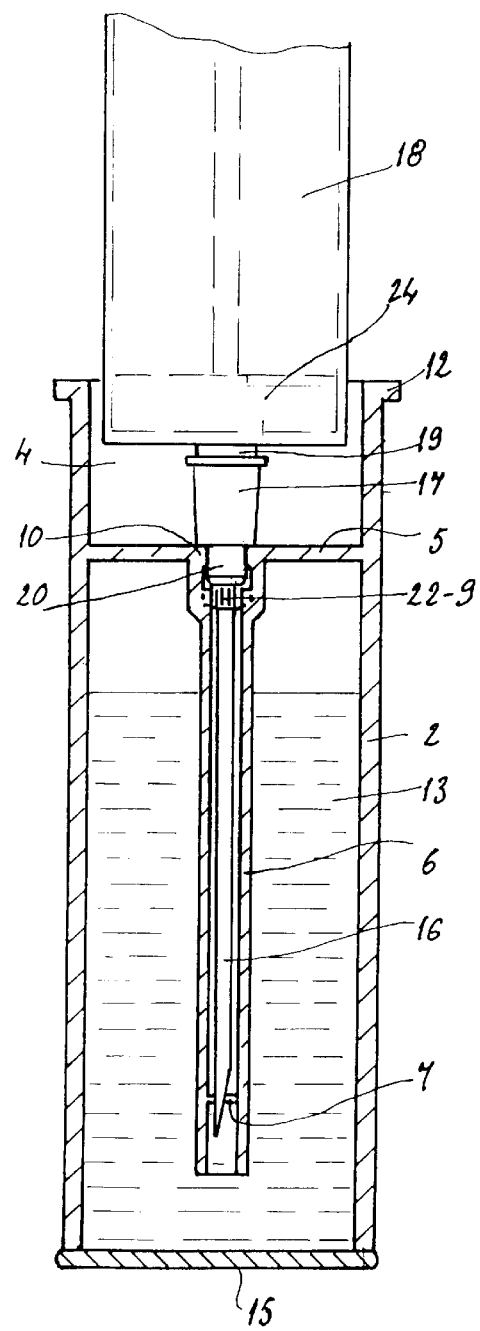

VIAL FOR PACKAGING A LIQUID FOR MEDICAL USE

A vial for packaging a liquid for medical use is a small reservoir, the volume of which varies from a few milliliters to a few tens of milliliters, and which is intended to contain in a sealed and sterile manner an active principle or a solvent (0.9% NaCl, 5% glucose). The reservoir is made of a material which is biocompatible with its content and of pharmaceutical grade. The material of which the reservoir is made may be glass or synthetic material. Glass vials are intended to be gradually phased out and replaced with vials made of synthetic material which are more practical to use.

The content of a vial is generally used to dilute active principles or to reconstitute powdered medicinal products.

The way in which a vial is used in the context of reconstitution is as follows:

- the operator disinfects the zone of the opening of the vial, then breaks the tearable element to gain access to the content thereof;
- the operator removes a sterile hypodermic needle from its packaging, attaches the needle to a syringe, and withdraws the rigid sheath that forms a needle protector;
- the operator sucks out a given volume of liquid from inside the vial, it being possible for this volume to be checked using the graduations on the syringe;
- once the liquid has been taken up into the syringe, the operator transfers this liquid into a bottle containing the powder or lyophilisate that is to be diluted. The bottle is sealed closed by an elastomer stopper that the syringe needle can perforate;
- after homogenization, the solution is drawn back up by the syringe;
- the product thus prepared is stored in the syringe fitted with its needle, can then be transferred to a drip bag or bottle, still using the needle by puncturing a sealed membrane provided for this purpose on the drip bag or bottle;
- after use, the needle is put back inside the needle protector to be discarded without the risk of needle stick injury.

This technique entails a great many elements for using the content of a vial: Needle housed inside a protector and packaged in sterile packaging, syringe, and vial containing the liquid. The number of operations to-be performed is high. The needle packaging has to be opened, the needle attached to the syringe, the needle protector removed, the vial disinfected, the vial broken with the risk of generating particles which may drop into the liquid contained therein, and the needle has to be introduced into a small-diameter hole.

This results in costs which are high both as regards the device itself and as regards its use.

The object of the invention is to provide a vial for packaging a liquid for medical use which is of an economical price, the use of which is simple, reliable and quick for the user.

To this end, the vial to which it relates comprises a tubular body made of synthetic material exhibiting two chambers which are isolated in a sealed manner by a puncturable membrane or a removable or tearable wall, one of which chambers contains the liquid and the other of which chambers contains a hypodermic needle, the pointed part of which points towards the puncturable membrane or removable or tearable wall, and the other end of which is fitted with means of connection to a syringe body.

Advantageously, the chamber containing the needle comprises a tube forming a needle holder closed by the membrane or the removable or tearable wall and exhibiting, at its end opening into the chamber containing the needle, an annular sealing bead. The needle is therefore packaged in the chamber provided for this purpose, the part forming the actual needle proper being inside the tube, and the end equipped with means of connection to a syringe body being outside the tube. In practice, the operator opens the chamber containing the needle, attaches the body of a syringe to it, and pushes down on the needle to puncture the membrane to gain communication with the chamber containing the liquid, or breaks the tearable wall corresponding to this membrane. The annular sealing bead seals the chamber containing the liquid closed. The operator can then use the syringe to draw up the desired amount of liquid, which is made easier by the fact that the tubular body made of synthetic material is deformable. After the contents of the syringe have been used in a conventional way, the operator can put the needle back inside the tube that forms the needle holder, which protects this needle while it is taken away to be destroyed.

According to one feature of the invention, the length of the tube intended to house the needle is at least equal to that of the needle, the membrane or the removable or tearable wall being located near to that end of the tube which faces towards the chamber containing the liquid and the bead located near the other end of the tube being intended to provide sealing around the means of connecting the needle to a syringe body.

Furthermore, the distance between the free end of the tube and the membrane or the removable or tearable wall is at least equal to the travel of the needle between a storage position and a position for withdrawing the liquid, in which position the pointed end of the needle passes through the membrane or the removable or tearable wall and the means of connecting the needle are gripped in the sealing bead. Under these conditions, the needle does not protrude from the end of the tube after the membrane has been punctured or the removable wall torn, which means that the risk of the wall of the vial being punctured accidentally by the point of the needle is eliminated. The translational movement of the needle is limited by a shoulder that this needle has in the zone of connection between the hypodermic needle itself and the means of connection of the needle, for example of the female Luer type, to the body of the syringe.

Advantageously, the tube comprises, near the sealing bead, means for preventing the needle from rotating, such as ribs or bosses intended to collaborate with complementary means borne by the needle. This feature makes the needle easier to attach to the syringe body by preventing the needle from turning at the same time as the syringe.

According to a preferred embodiment of this vial, the tube intended to house the needle is secured to a transverse wall, the periphery of which is secured to the interior wall of the tubular body. The tube advantageously forms a single piece with the interior wall of the tubular body.

According to a first embodiment of this vial, the tubular body, the wall separating the two chambers and the needle holder are made as one piece of synthetic material obtained by moulding.

In this case, for example, the chamber containing the liquid is closed off by a thermal weld after the body has been filled with the liquid and flattened, and the chamber containing the needle, the edge of which is delimited by a flange, is closed by a film seal, such as a vapour-permeable film, fixed by hot welding or by a stopper made of synthetic material sealed on by screw-fastening or snap-fastening. Closure using a vapour-permeable film allows the chamber containing the needle to be sterilized.

According to one other feature of the invention, on the one hand, the wall separating the two chambers and the needle holder are made as one piece of synthetic material obtained by moulding and, on the other hand, the tubular body consists of a tube of synthetic material which is extruded or made from two films of possibly thermoformed synthetic material, fixed by welding to the wall separating the two chambers, and the two ends of which are closed by thermal welds after the two chambers have been formed, the chamber containing the liquid has been filled, and the needle has been placed in the other chamber.

In such a case it is possible to make the tubular body from a material that is far more flexible than the wall separating the two chambers and the needle holder, and for the ends of the two chambers, and particularly the end of the chamber containing the liquid, to be given a shape, for example, in the form of a V which makes it possible to limit the residual volume of liquid inside this chamber as far as possible.

In any case, the invention will be clearly understood with the aid of the description which follows with reference to the appended diagrammatic drawing which, by way of non-limiting examples, depicts a number of embodiments of vial:

FIG. 1 is a view in cross section and in an exploded position of the various constituent parts of the vial;

FIG. 2 is a view in longitudinal section of the same vial in the closed position;

FIGS. 3 to 5 are three views in section depicting three phases in the use of this vial;

Figure 5:
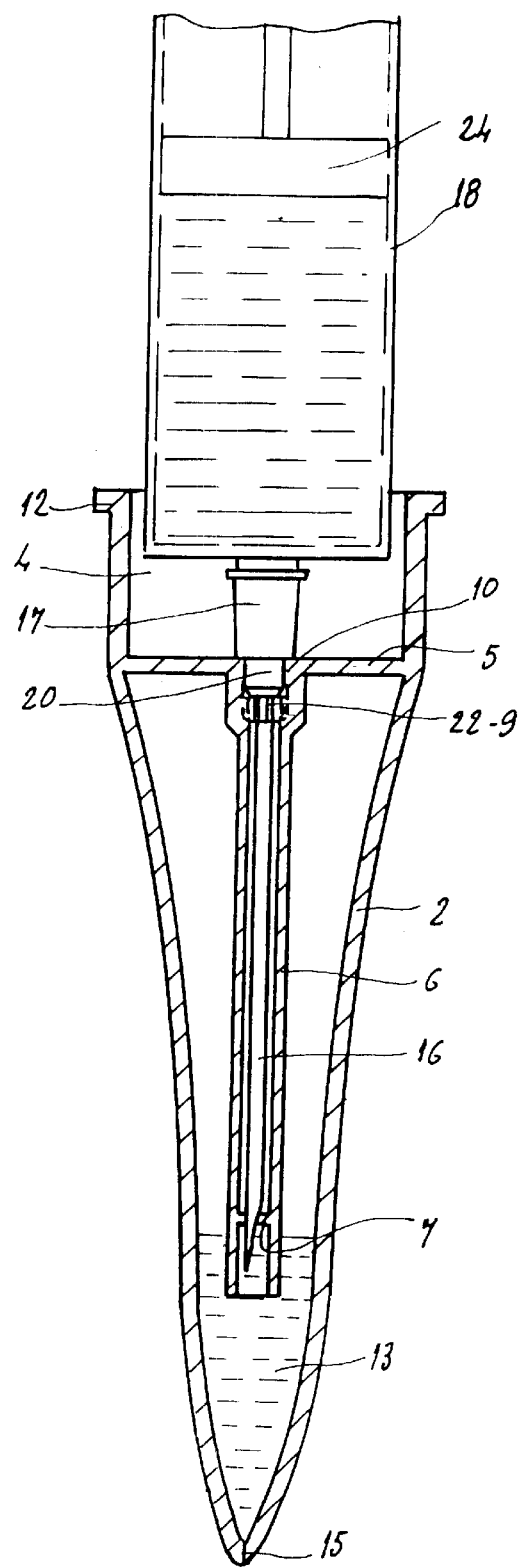

The vial depicted in FIG. 1 comprises a cylindrical tubular body 2 made of synthetic material, exhibiting two chambers, a lower chamber 3 and an upper chamber 4, which are separated from one another in a sealed fashion by a disc-shaped partition 5. Extending at the centre of the tubular body, and inside the chamber 3 from this partition 5 is a tube 6 which opens into the chamber 4 and which, near to its end located in the chamber 3, has a membrane 7 or tearable or removable wall. The inside of the tube 6 communicates with the chamber 4. The end of the tube 6 which is located on the same side as the chamber 4 comprises a widened part 8, in the bottom of which a system of longitudinal grooves/ribs 9 is located. This widened part 8 is connected to the chamber 4 by an annular bead 10. The tubular body 2 comprises an end located on the same side as the chamber 4, surrounded by a flange 12.

In the embodiment depicted in FIG. 1, the cylinder 2, the partition 5 and the tube 6 consist of a single piece of synthetic material obtained by moulding. This piece is transparent and the wall of the tubular body has good flexibility allowing it to deform. After the chamber 3 has been filled with a liquid 13, this chamber is sealed by a thermal weld 15, after the body has been flattened. The chamber 4 and the tube 6 are intended to act as a housing for a hypodermic needle 16 equipped with a device 17, of the female Luer type, for connection to a syringe 18, the outlet orifice of which is fitted with a male Luer coupling 19. The connection zone 17 of the needle 16 is extended on the needle side by a part 20 intended to be engaged with sealing in the annular bead 10, and by a system of grooves/ribs 22 which is intended to collaborate with the system of grooves/ribs 9 belonging to the tube 6. The length of the hypodermic needle is such that, in the position of storage of the needle in the chamber 4 and the tube 6, the needle is engaged in the tube 6, with its sharp end near the membrane or tearable wall 7. After the needle has been placed in the chamber 4 and the tube 6, the chamber 4 is sealed with peelable and vapour-permeable paper 23, attached by thermal welding.

The vial is used as follows.

The operator first of all pulls of the paper 23 to access the needle. He positions the body of the syringe 18 in such a way as to introduce the male coupling 19 into the female coupling 17 of the needle, the plunger 24 of the syringe being in the forward position. The pressure exerted by the syringe on the needle causes a translational movement of the needle which punctures the membrane 7. The movement of the needle is limited by the widened part 17 pressing against the partition 5. In this position, the annular bead 10 surrounds the part 20 of the needle in a sealed fashion and the grooves/ribs 22 of the needle are engaged in the grooves/ribs system 9 belonging to the tube 6. The needle is thus immobilized in terms of translation and in terms of rotation and this makes it possible, through a rotational movement, to couple the syringe body and the needle. In this position, the sharp end of the needle has passed through the wall 7, but remains inside the tube 6, which avoids any risk of puncturing the vial. This position is depicted in FIG. 4.

The operator then pulls back on the plunger 24, drawing liquid into the syringe body 8. This suction is made possible by the flexibility of the material of which the tubular body 2 is made, as shown in FIG. 5 which is a view in section offset by 90° with respect to the previous views. After the desired amount of liquid has been transferred into the syringe, this syringe can be used in the conventional way. Once the syringe has been used, the needle can be placed back inside the tube 6, which then acts as a needle protector before this needle is destroyed.

Figure 6:
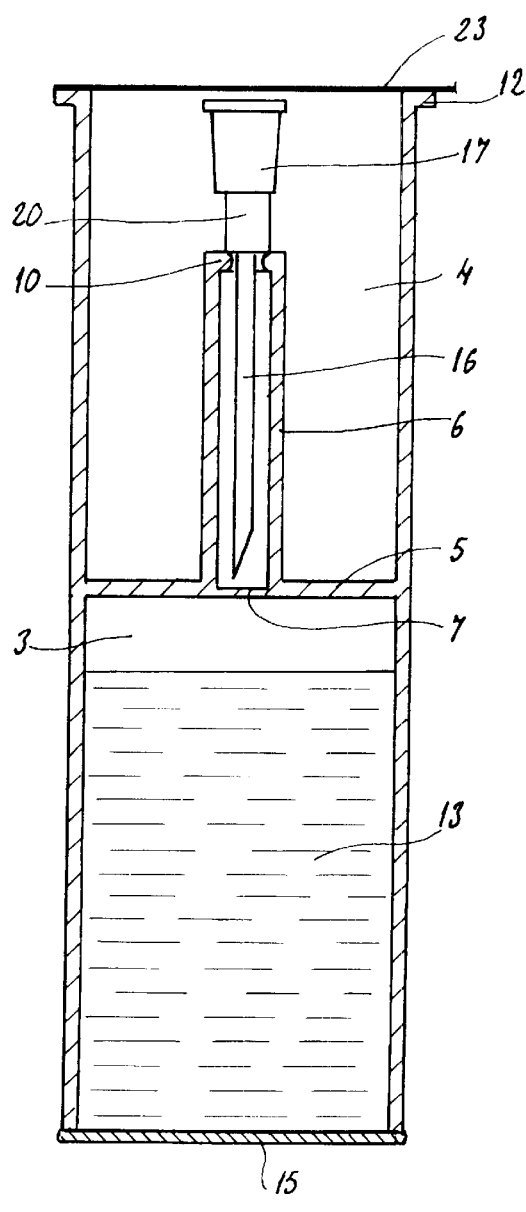
FIGS. 6 and 7 are two views in cross section and in the filled position of two other vials.

FIG. 6 depicts an alternative form of embodiment of this vial, in which the same elements are denoted by the same references as previously. In this case, the tube 6 is no longer housed in the chamber 3, but in the chamber 4. This structure is justified by the fact that, in this embodiment, the vial is intended to contain a short hypodermic needle 16. In this case, the liquid is transferred from the vial into the syringe with the vial in the inverted position.

Figure 7:
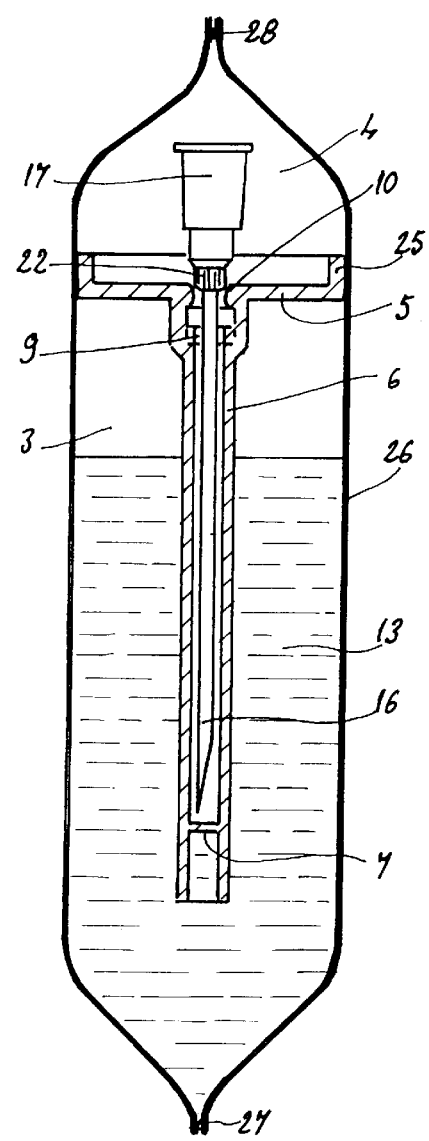

FIG. 7 depicts another embodiment of the vial according to the invention, in which the same elements are denoted by the same references as previously. In this case, the partition 5 and the tube 6 consist of a piece of moulded synthetic material. The partition 5 comprises a peripheral flange 25. The tubular body 26 consists of a tube of extruded synthetic material, which is welded to the flange 25 and which is sealed by welds 27, 28 to respectively seal the chamber 3 and the chamber 4.

As is apparent from the foregoing, the invention provides a great improvement to the existing state of the art by providing a vial for packaging a liquid for medical use which can also be used for packaging the needle used to transfer the liquid from the vial. This vial has a simple structure, is of an economical cost, and, given its conditions of use, affords perfect safety both to the operators and to the patients to be treated with the liquid or product prepared from this liquid.

As goes without saying, the invention is not restricted to the mere embodiments of this vial which have been described hereinabove by way of examples; on the contrary, it encompasses all variations thereon. Thus, in particular, the tubular body made of synthetic material could be made from two sheets of synthetic material, possibly thermoformed, while the vial need not comprise a tube for housing the needle, the partition between the two chambers could be not circular, or the tube could be not centred, without this in any way departing from the scope of the invention.

What is claimed is:

1. Vial for packaging a liquid for medical use, comprising a tubular body made of synthetic material having two chambers which are isolated in a sealed manner by a puncturable membrane or a removable or tearable wall, one of which chambers contains the liquid and the other of which chambers contains a hypodermic needle, the pointed part of which points towards the puncturable membrane or removable or tearable wall, and the other end of which is fitted with means of connection to a syringe body, the chamber containing the needle comprising a tube forming a needle holder closed by the membrane or the removable or tearable wall and exhibiting, at its end opening into the chamber containing the needle, an annular sealing bead, the length of the tube intended to house the needle is at least equal to that of the needle, the membrane or the removable or tearable wall being located near to that end of the tube which faces towards the chamber containing the liquid and the bead located near the other end of the tube being intended to provide sealing around the means of connecting the needle to a syringe body, the vial being characterized in that the distance between the free end of the tube intended to house the needle and the membrane or the removable or tearable wall is at least equal to the travel of the needle between a storage position and a position for withdrawing the liquid, in which position the pointed end of the needle passes through the membrane or the removable or tearable wall and the means of connecting the needle are gripped in the sealing bead.

2. Vial according to claim 1, characterized in that the tube comprises, near the sealing bead, means for preventing the needle from rotating intended to collaborate with complementary means borne by the needle.

3. Vial according to claim 1, characterized in that the tube intended to house the needle is secured to a transverse wall, the periphery of which is secured to the interior wall of the tubular body.

4. Vial according to claim 1, characterized in that the tubular body is made of a flexible material that allows it to deform when liquid is being drawn up.

5. Vial according to claim 1, characterized in that the tubular body, the wall separating the two chambers and the needle holder are made as one piece of synthetic material obtained by moulding.

6. Vial according to claim 5, characterized in that the chamber containing the liquid is closed off by a thermal weld after the body has been filled with the liquid and flattened, and the chamber containing the needle, the edge of which is delimited by a flange, is closed by a film seal fixed by hot welding or by a stopper made of synthetic material sealed on by screw-fastening or snap-fastening.

7. Vial according to claim 1 characterized in that the wall separating the two chambers and the needle holder are made as one piece of synthetic material obtained by moulding and the tubular body consists of a tube of synthetic material which is extruded, or made from two films of thermoformed synthetic material, fixed by welding to the wall separating the two chambers, and the two ends of which are closed by thermal welds after the two chambers have been formed, the chamber containing the liquid has been filled, and the needle has been placed in the other chamber.

8. Vial according to claim 2, characterized in that the means for preventing the needle from rotating is achieved by ribs or bosses.

* * * * *